US011589979B2

(12) United States Patent
Pankin (10) Patent No.: US 11,589,979 B2
(45) Date of Patent: Feb. 28, 2023

(54) INTRAOCULAR LENS

(71) Applicant: Carl Zeiss Meditec AG, Jena (DE)

(72) Inventor: Dmitry Pankin, Berlin (DE)

(73) Assignee: Carl Zeiss Meditec AG, Jena (DE)

(*) Notice: Subject to any disclaimer, the term of this patent is extended or adjusted under 35 U.S.C. 154(b) by 0 days.

(21) Appl. No.: 17/830,909

(22) Filed: Jun. 2, 2022

(65) Prior Publication Data

US 2022/0287822 A1    Sep. 15, 2022

Related U.S. Application Data

(63) Continuation of application No. PCT/EP2019/086603, filed on Dec. 20, 2019.

(51) Int. Cl.
*A61F 2/16* (2006.01)
*A61F 2/00* (2006.01)

(52) U.S. Cl.
CPC ........ *A61F 2/16* (2013.01); *A61F 2002/0081* (2013.01); *A61F 2002/1689* (2013.01)

(58) Field of Classification Search
CPC ................ A61F 2/16; A61F 2002/0081; A61F 2002/1689
See application file for complete search history.

(56) References Cited

U.S. PATENT DOCUMENTS

| | | | |
|---|---|---|---|
| 6,129,760 | A | 10/2000 | Fedorov et al. |
| 10,219,893 | B2 | 3/2019 | Currie et al. |
| 2005/0107875 | A1 | 5/2005 | Cumming |

FOREIGN PATENT DOCUMENTS

| | | |
|---|---|---|
| FR | 2 749 161 A1 | 12/1997 |
| WO | 01/89425 A1 | 11/2001 |
| WO | 2006/033984 A1 | 3/2006 |

OTHER PUBLICATIONS

International Search Report of the European Patent Office dated Oct. 5, 2020 for international application PCT/EP2019/086603 on which this application is based.
Translation and Written Opinion of the International Searching Authority dated Oct. 5, 2020 for international application PCT/EP2019/086603 on which this application is based.
Translation and International Preliminary Report on Patentability of the International Preliminary Examining Authority dated May 17, 2022 for international application PCT/EP2019/086603 on which this application is based.

*Primary Examiner* — William H Matthews
(74) *Attorney, Agent, or Firm* — Walter Ottesen, P.A.

(57) ABSTRACT

An intraocular lens includes an optical body having a geometric center point through which a longitudinal axis extends and a second main axis extends as a transverse axis. The transverse axis is perpendicular to the longitudinal axis. A flat first and a second haptic body are each adjacent to the optical body. The first and second haptic bodies are arranged point-symmetrically to the geometric center. An outer radius of the intraocular lens about the geometric center and a radial distance from the geometric center to an intersection point of the transverse axis with a circumferential line of the intraocular lens have a ratio to one another from 1:0.5 to 1:0.9. The first haptic body has a recess on the left of the longitudinal axis and another recess on the right thereof. The two recesses each have a length and a width, the length being greater than the width.

7 Claims, 5 Drawing Sheets

INTRAOCULAR LENS

CROSS REFERENCE TO RELATED APPLICATION

This application is a continuation application of international patent application PCT/EP2019/086603, filed Dec. 20, 2019, designating the United States, and the entire content of the international application is incorporated herein by reference.

TECHNICAL FIELD

The disclosure relates to an intraocular lens which has an optics body with an optical axis and a plate-like haptic body adjoining the optics body.

BACKGROUND

An intraocular lens is intended as a replacement for a natural eye lens when the natural eye lens no longer enables good vision due to clouding or hardening. Each intraocular lens has an optics body through which light rays can reach a retina of a patient's eye. So that the optics body can be arranged as centrally as possible in a capsular bag of the patient's eye, spacers that come into contact with the surrounding capsular bag adjoin the optics body. The spacers, which are also referred to as haptic bodies, are often C-shaped or J-shaped. Such haptic bodies are very narrow, so that it is possible to very strongly fold the intraocular lens and to insert it into the capsular bag through a very small incision.

However, it can be advantageous for an intraocular lens to be provided with a haptic body that is configured like a plate. Such an intraocular lens can be handled easily by the surgeon immediately after implantation into a capsular bag and be centered in the capsular bag, with only a small risk of damaging the optics body when handling the haptic body. Since a plate-like haptic body has a relatively large outer periphery, a relatively large contact surface with the inner wall of a capsular bag is also achievable. This means that the position of the intraocular lens in the capsular bag is stable even over a long period of time.

The disadvantage, however, is that with a relatively small capsular bag, an intraocular lens with a plate-like haptic body is under great mechanical stress. This can lead to such an intraocular lens bending along its longitudinal axis. The result can be an axial shift of the optics body in the capsular bag, as a result of which the focal point of the intraocular lens is displaced to in front of or behind the retina, which is associated with a loss of sharpness. If the rear of the intraocular lens is provided with a PCI edge to prevent secondary cataracts, the intraocular lens might no longer rest against the rear wall of the capsular bag as intended after such an axial shift. As a result, the cells that form a secondary cataract can penetrate into the central region of the rear wall of the capsular bag and cause renewed clouding of vision. An intraocular lens with a plate-like haptic that has been inserted in a capsular bag that is too small can deform here in such a way that the optics body undergoes astigmatic distortion.

Intraocular lenses with a haptic body are described, for example, in WO 01/89425 A1 and WO 2006/033984 A1.

SUMMARY

It is an object of the disclosure to disclose an intraocular lens with a plate-like haptic body that enables good vision even with a relatively small capsular bag.

The object can, for example, be achieved by an intraocular lens including: an optics body having a geometric center M through which a first main axis runs as a longitudinal axis L of the intraocular lens and a second main axis runs as a transverse axis Q; the transverse axis Q being arranged perpendicular to the longitudinal axis L of the intraocular lens; a plate-like first haptic body adjoining the optics body; a plate-like second haptic body adjoining the optics body; the first haptic body and the second haptic body being disposed point-symmetrically to the geometric center M; the intraocular lens defining a circumferential line, an outer radius RA of the intraocular lens around the geometric center M, and a radial distance A1 from the geometric center M to a point of intersection of the transverse axis Q with the circumferential line; the outer radius RA and the radial distance A1 having a ratio with respect to each other lying in a range of 1:0.5 to 1:0.9; the first haptic body defining at least two first cutouts including a first-first cutout and a second-first cutout; the first-first cutout being disposed on a left-hand side of the longitudinal axis; the second-first cutout being disposed on a right-hand side of the longitudinal axis; the first-first cutout and the second-first cutout each having a corresponding first cutout length and a corresponding first cutout width, wherein the corresponding first cutout lengths are greater than the corresponding first cutout widths; the at least two first cutouts each having a first cutout centroid, wherein the first cutout centroids can be connected by a line forming a first circular arc having a first radius R1 around a first center M1 arranged on the longitudinal axis L; the first haptic body defining at least two second cutouts including a first-second cutout and a second-second cutout; the first-second cutout being disposed on the left-hand side of the longitudinal axis L; the second-second cutout being disposed on the right-hand side of the longitudinal axis L; the first-second cutout and the second-second cutout each having a corresponding second cutout length and a corresponding second cutout width, wherein the corresponding second cutout lengths are greater than the corresponding second cutout widths; the at least two second cutouts each having a second cutout centroid, wherein the second cutout centroids can be connected by a line forming a second circular arc having a second radius R2 around the first center M1; and, the second radius R2 being smaller than the first radius R1.

According to an embodiment of the disclosure, the intraocular lens has:
- an optics body with a geometric center through which a first main axis runs as the longitudinal axis and a second main axis runs as the transverse axis, wherein the transverse axis is arranged perpendicular to the longitudinal axis of the intraocular lens,
- a plate-like first haptic body adjoining the optics body and a plate-like second haptic body adjoining the optics body, wherein the first haptic body and the second haptic body are arranged point-symmetrically to the optical axis,
- wherein an outer radius of the intraocular lens around the geometric center and a radial distance from the geometric center to a point of intersection of the transverse axis with a circumferential line of the intraocular lens have a ratio with respect to each other which is in the range of 1:0.5 to 1:0.9,
- wherein in the first haptic body at least two first cutouts are present, wherein the one first cutout is present on the left-hand side of the longitudinal axis and the further first cutout is present on the right-hand side of the longitudinal axis, wherein the two first cutouts have a respective first cutout length and a first cutout width, wherein the first cutout length is greater than the first cutout width, wherein the first cutouts each have a centroid, wherein these respective centroids can be connected by a line which forms a first circular arc having a first radius around a first center which is arranged on the longitudinal axis, wherein in the first haptic body at least two second cutouts are present, wherein the one second cutout is present on the left-hand side of the longitudinal axis and the further second cutout is present on the right-hand side of the longitudinal axis, wherein the two second cutouts have a respective second cutout length and a second cutout width, wherein the second cutout length is greater than the second cutout width, wherein the second cutouts each have a centroid, wherein these respective centroids can be connected by a line which forms a second circular arc having a second radius around the first center, wherein the second radius is smaller than the first radius.

The intraocular lens thus has an optics body which, viewed in a top view, has a geometric center. The geometric center of the intraocular lens is usually a point intersected by an optical axis of the optics body. A first main axis of the intraocular lens and a second main axis of the intraocular lens can be specified in a top view of the intraocular lens. The first main axis is a longitudinal axis which extends in the direction of greatest extent or in the longitudinal direction of the intraocular lens. In the case of the intraocular lens according to the disclosure, a second main axis, which represents a transverse axis of the intraocular lens, likewise extends perpendicularly to the first main axis in the top view.

A plate-like first haptic body and a plate-like second haptic body adjoin the optics body. Both haptic bodies are arranged point-symmetrically to the geometric center of the intraocular lens. The first haptic body and the second haptic body preferably extend along the longitudinal axis.

A circumference with an outer radius around the geometric center can be placed around the intraocular lens in the top view. The outer radius can be placed in a ratio to a radial distance formed from the geometric center to a point of intersection of the transverse axis with a circumferential line of the intraocular lens. In the intraocular lens according to the disclosure, this ratio of the outer radius to the radial distance lies in a range from 1:0.5 to 1:0.9, preferably in the range from 1:0.5 to 1:0.8, or preferably in the range from 1:0.5 to 1:0.7, or preferably in the range from 1:0.5 to 1:0.6. The intraocular lens thus extends more along the longitudinal axis than along the transverse axis.

The intraocular lens has at least two first cutouts in the first haptic body. The one first cutout is arranged on the left-hand side of the longitudinal axis, and the further first cutout is arranged on the right-hand side of the longitudinal axis. Furthermore, the intraocular lens has at least two second cutouts in the first haptic body, wherein the one second cutout is arranged on the left-hand side of the longitudinal axis and the further second cutout is arranged on the right-hand side of the longitudinal axis. The intraocular lens in the first haptic body preferably also has at least one third cutout, wherein this third cutout intersects the longitudinal axis. The third cutout has a third cutout length and a third cutout width, wherein the third cutout length is greater than the third cutout width.

The intraocular lens preferably has at least two first cutouts in the second haptic body. The one first cutout is arranged on the left-hand side of the longitudinal axis, and the further first cutout is arranged on the right-hand side of the longitudinal axis. Furthermore, the intraocular lens has at least two second cutouts in the second haptic body, wherein the one second cutout is arranged on the left-hand side of the longitudinal axis and the further second cutout is arranged on the right-hand side of the longitudinal axis. The intraocular lens in the second haptic body preferably also has at least one third cutout, wherein this third cutout intersects the longitudinal axis. The third cutout has a third cutout length and a third cutout width, wherein the third cutout length is greater than the third cutout width.

The cutouts cause elastic deformation of the first haptic body or second haptic body in the direction of the optics body when a compressive force is directed in the direction of the longitudinal axis and parallel to the longitudinal axis of the intraocular lens, that is, from the first haptic body or second haptic body in the direction of the optics body. A cutout can be viewed as an elastic spring in an equivalent circuit diagram. Since not only first cutouts but also second cutouts are provided, which can each deform, wherein the first cutouts are arranged on a circular arc having a first radius around a center and the second cutouts are arranged on a circular arc having a second radius around the center, which is smaller than the first radius, this means a series connection of elastic springs in the event of a compressive force from the first haptic body or second haptic body in the direction of the optics body. The entire spring travel is thus divided between the first cutouts and second cutouts, with the result that each cutout experiences only a relatively short spring travel. With a relatively small capsular bag, the haptic can thus be significantly shortened in length, that is, along its longitudinal axis.

Since the respective cutout length of a first cutout or a second cutout is greater than the respective cutout width, the haptic body still has good torsional stiffness, so that when a compressive force is directed onto the haptic body in the direction of the longitudinal axis and parallel to the longitudinal axis, the optics body is not deformed and no astigmatic distortion of the optics body occurs. Since there is no deformation of the optics body, a good fit of the optics body against the inner rear wall of the capsular bag is ensured, so that a PCI edge on the intraocular lens can continue to work well and formation of secondary cataracts is avoided.

The first cutout or the second cutout is preferably configured in the form of a slot. A ratio of the cutout length to the cutout width of significantly greater than 1 can thus be achieved, and great elasticity in the longitudinal axis of the intraocular lens and simultaneously a high torsional stiffness are thus achieved. Compressive forces on a circumferential wall of the haptic body of the intraocular lens can be evenly absorbed.

In addition, the production of a slot is relatively simple from a mechanical point of view.

It can be advantageous if the intraocular lens is made from a single material. This means that no additional elements such as wires need to be integrated for greater stiffness in one dimension. An intraocular lens made from a single material also enables homogeneous mechanical properties with great accuracy. Strong folding with an injector for a microincision is thus readily possible, wherein uniform unfolding in the capsular bag is achievable within a relatively short time.

The first cutout or second cutout is preferably present only within the first haptic body and/or only within the second haptic body and does not reach an outer periphery of the first haptic body and/or second haptic body. In this way, a higher torsional stiffness of the intraocular lens around its longitudinal axis can additionally be ensured.

The first cutout and/or second cutout can each have a cutout width in a range from 0.05 mm to 0.8 mm, preferably from 0.05 mm to 0.4 mm, and particularly preferably from 0.1 mm to 0.3 mm. This makes it possible to achieve a high elasticity of the haptic body in the longitudinal axis of the intraocular lens and simultaneously a high torsional stiffness.

In a further embodiment, the intraocular lens has an upper side and a lower side, and the first cutout or second cutout extends in the longitudinal cross section from the upper side to the lower side. A cutout is thus an opening or a hole, with the result that a very high elasticity of the haptic body in the longitudinal axis of the intraocular lens and simultaneously a high torsional stiffness are possible.

The first cutout or second cutout preferably has a greater width in the longitudinal cross section on the upper side of the intraocular lens than on the lower side of the intraocular lens. As a result, the flexural stiffness is lower on the upper side than on the lower side, so that bending can take place along the longitudinal axis in a defined direction, that is, toward the upper side. The result is a greater certainty that the rear wall of the optics body rests reliably against the inside of the capsule wall and no axial shift of the intraocular lens occurs along the optical axis.

BRIEF DESCRIPTION OF THE DRAWINGS

The invention will now be described with reference to the drawings wherein.

DESCRIPTION OF THE PREFERRED EMBODIMENTS

Figure 1:
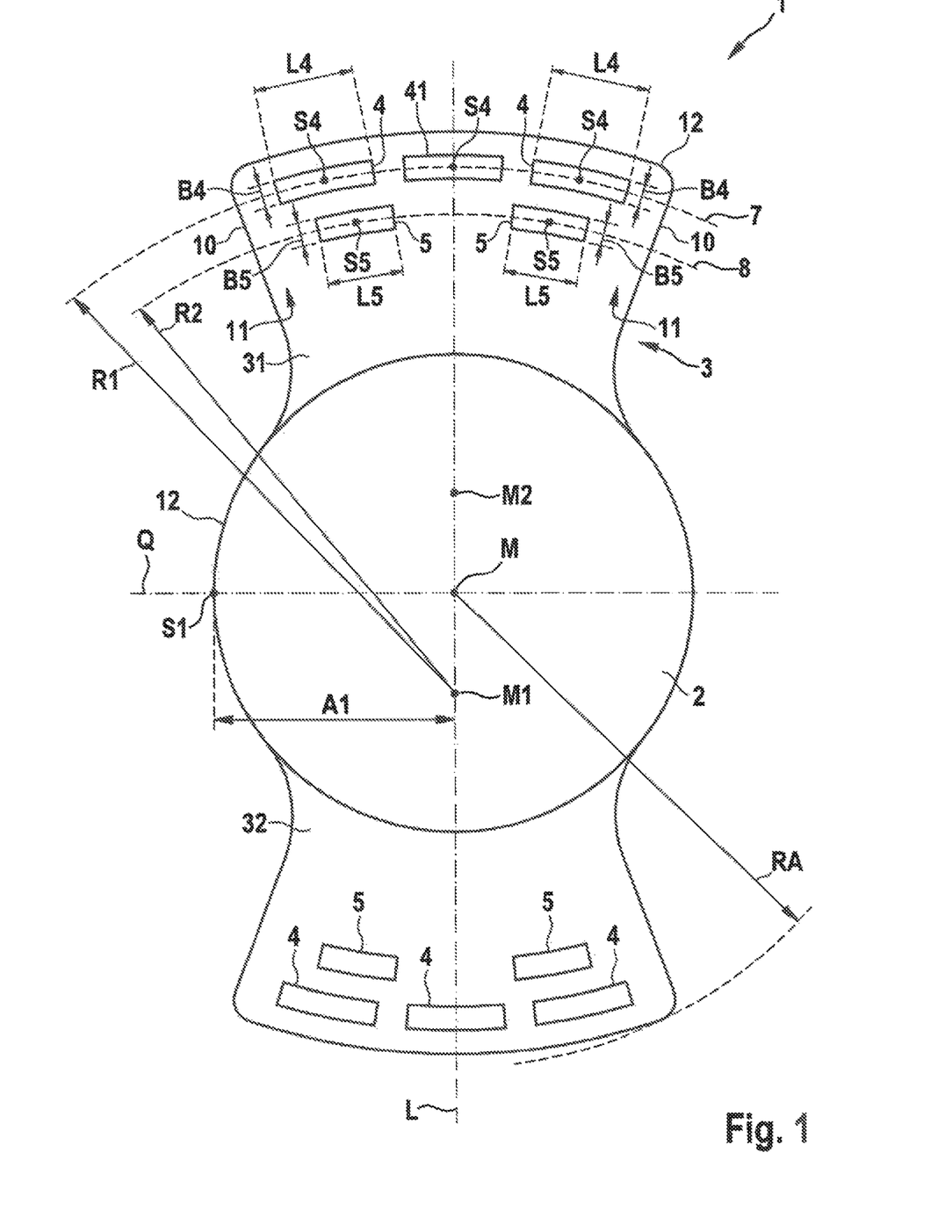
FIG. 1 shows a schematic illustration of an intraocular lens according to a first embodiment in a top view.

FIG. 1 shows an intraocular lens 1 having an optics body 2 with an optical axis A, which extends perpendicularly to the plane of the drawing and perpendicularly to a longitudinal axis L of the intraocular lens 1. A plate-like haptic body 3, which is formed in one piece with the optics body 2, adjoins the optics body 2. The haptic body 3 has a first haptic body 31 and a second haptic body 32, wherein the first haptic body 31 and the second haptic body 32 are arranged point-symmetrically to the geometric center M.

If a circumference around the intraocular lens 1 is formed around the geometric center M, this circumference has an outer radius RA. A radial distance A1 is defined such that it forms the distance between the geometric center M and a point of intersection S1 of the transverse axis Q with a circumferential line 12 of the intraocular lens 1. The ratio of the outer radius RA to the radial distance A1 is important, which is in the range from 1:0.5 to 1:0.9. This describes an intraocular lens 1 which has a greater extension along the longitudinal axis L than along the transverse axis Q. The problem with such an intraocular lens is that it can deform in a relatively small capsular bag in such a way that it bends along its longitudinal axis. This can lead to an axial shift of the optics body in the capsular bag or to astigmatic distortion of the optics body.

In order to avoid these consequences, the intraocular lens according to the disclosure has in the first haptic body 31 a first cutout 4 on the left-hand side of the longitudinal axis L and a further first cutout 4 on the right-hand side of the longitudinal axis L. The two first cutouts 4 are arranged symmetrically to the longitudinal axis L. In addition, the first haptic body 31 has a second cutout 5 on the left-hand side of the longitudinal axis L and a further second cutout 5 on the right-hand side of the longitudinal axis L. The two second cutouts 5 are arranged symmetrically to the longitudinal axis L.

The first cutout 4 has a first cutout length L4 and a first cutout width B4, wherein the first cutout length L4 is greater than the first cutout width B4. Each of the first cutouts 4 has a first centroid S4. The intraocular lens 1 according to the disclosure is configured in such a way that the centroids S4 of the first cutouts 4 can be connected by a line which forms a first circular arc 7 having a first radius R1 around a center M1. The center M1 is arranged on the longitudinal axis L. In a preferred embodiment, the center M1 lies at the same position as the geometric center M of the intraocular lens 1.

The second cutout 5 has a second cutout length L5 and a second cutout width B5, wherein the second cutout length L5 is greater than the second cutout width B5. Each of the second cutouts 5 has a second centroid S5, wherein these centroids S5 can be connected by a line that forms a second circular arc 8 having a second radius R2 around the center M1. The second radius R2 is smaller than the first radius R1, with the result that the second cutouts 5 are arranged closer to the optics body 2 than the first cutouts 4.

In this first embodiment, the first cutouts 4 and the second cutouts 5 are configured in the manner of slots. However, they can also be configured to have other geometries, for example triangular or drop-shaped, see FIG. 2. At least one third cutout 41 can also be provided between or next to the two first cutouts 4, with the centroid S4 of the third cutout likewise lying on the circular arc 7, see FIG. 1, wherein the third cutout intersects the longitudinal axis L. The third cutout 41 has a third cutout length and a third cutout width, wherein the third cutout length is greater than the third cutout width. An additional cutout 9 with a different geometry than the two first cutouts 4 can also be provided between the first cutouts 4, see FIG. 2, wherein it is possible for its centroid S9 not to be located on the circular arc 7.

Figure 2:
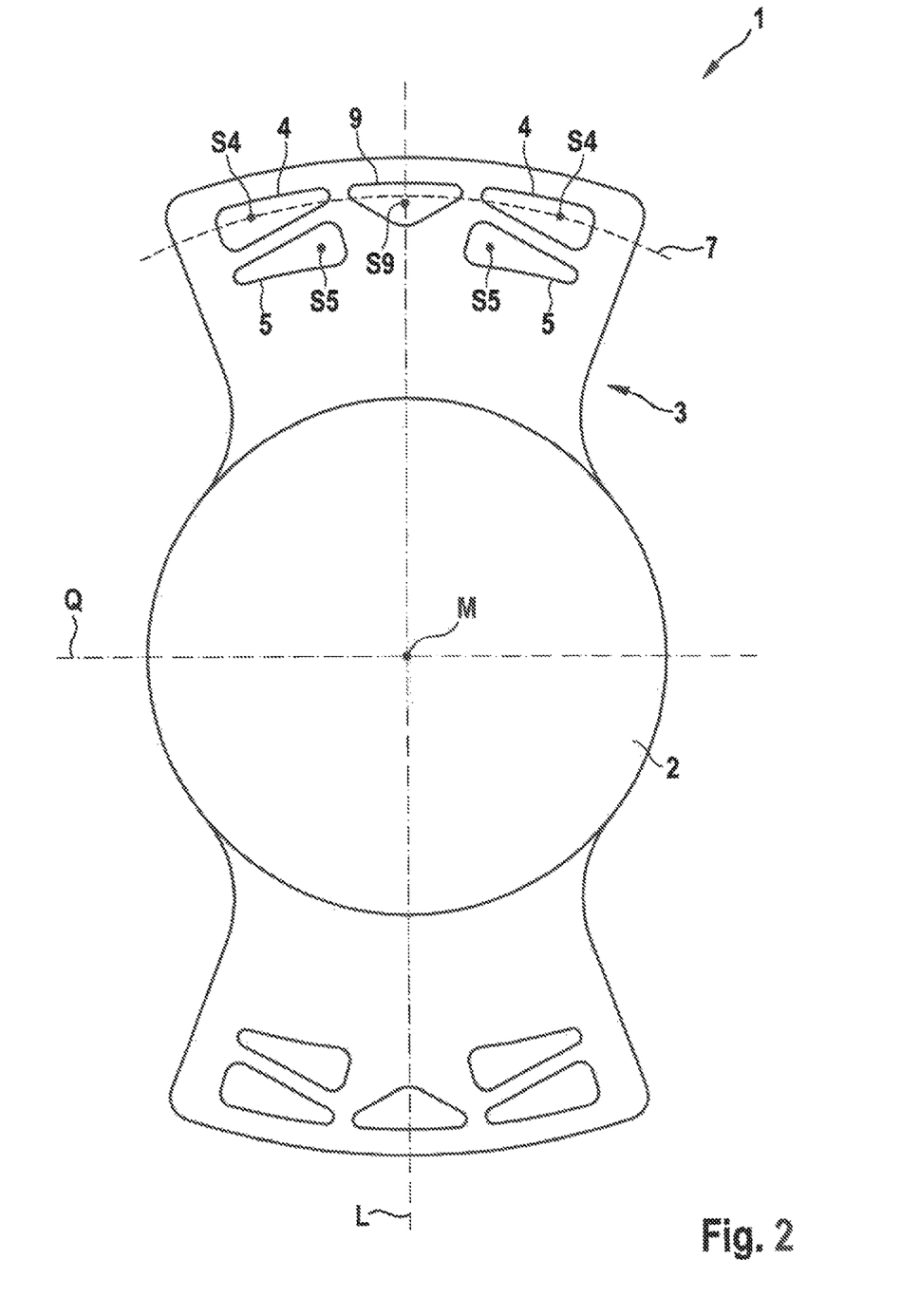
FIG. 2 shows a schematic illustration of an intraocular lens according to a second embodiment in a top view.

In the case of the intraocular lens 1 illustrated in FIGS. 1 and 2, the cutouts 4, 5 are provided in the first haptic body 31 and in the second haptic body 32. In the case of the cutouts 4, 5 which are located in the second haptic body 32, the respective centroids of the cutouts 4, 5 can likewise be connected by a line which forms a circular arc having a radius around a center. In the embodiment shown in FIG. 1, the associated center for the second haptic body 32 is the center M2.

In the intraocular lens 1 shown in FIG. 1, the second cutouts 5 are configured in the form of slots in the same way as the first cutouts 4. It is possible for at least one additional second cutout 5 to be provided between the second cutouts 5.

It can be advantageous if the cutouts 4, 5 are provided only within the first haptic body 31 or second haptic body 32 and do not reach an outer periphery 10 of the first haptic body 31 or second haptic body 32. This leaves a peripheral zone 11 at the first haptic body 31 or second haptic body 32 between the cutouts 4, 5 and the outer periphery 10 of the first haptic body 31 or second haptic body 32, with the result that a relatively high torsional stiffness of the first haptic body 31 or second haptic body 32 about the longitudinal axis L is achievable. A width of the peripheral zone 11 and thus a distance between the cutouts 4, 5 and the outer periphery 10 of the first haptic body 31 or second haptic body 32 is preferably the absolute value of the width B4 of the first cutout 4 or the width B5 of the second cutout 5. The width of the peripheral zone 11, that is, the distance between the cutouts 4, 5 and the outer periphery 10 of the first haptic body 31 or second haptic body 32, particularly preferably attains an absolute value in the range of once to twice the width B4 of the first cutout 4 or in the range of once to twice the width B5 of the second cutout 5.

Figure 3:
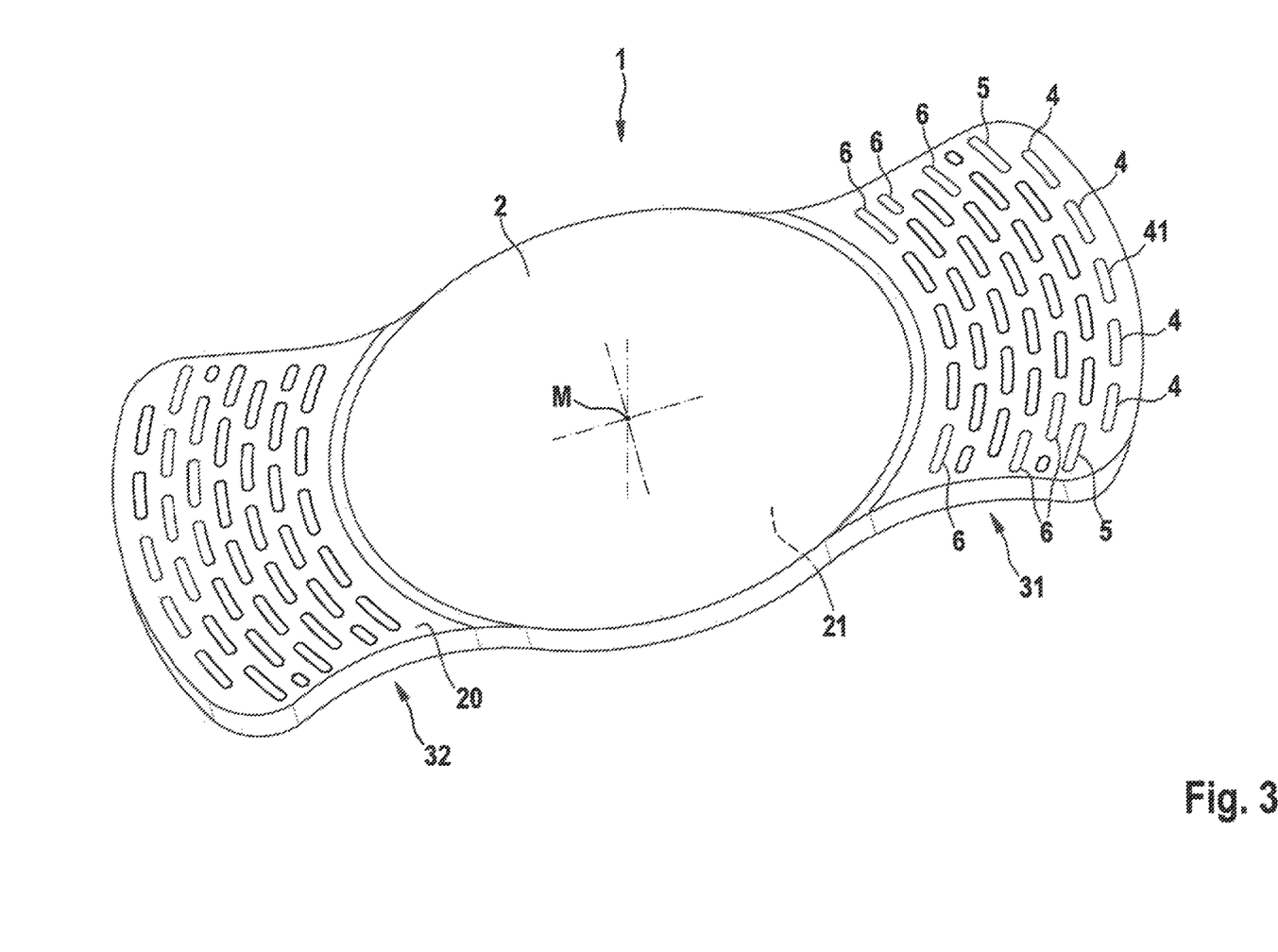
FIG. 3 shows an intraocular lens according to a third embodiment in a perspective view.
Figure 4A:
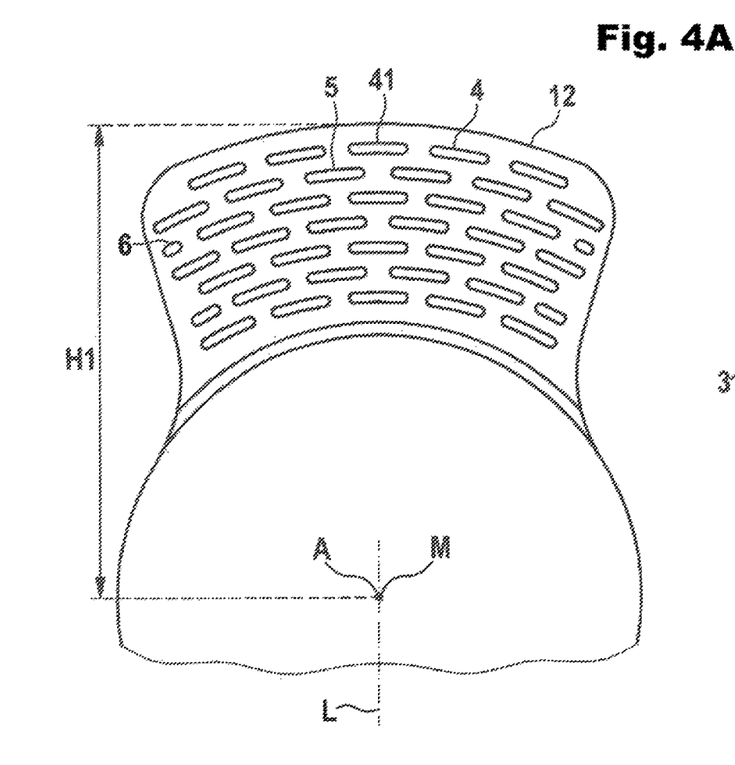
FIG. 4A shows a schematic illustration of a part of an intraocular lens according to the third embodiment in a top view in a relaxed state.
Figure 4B:
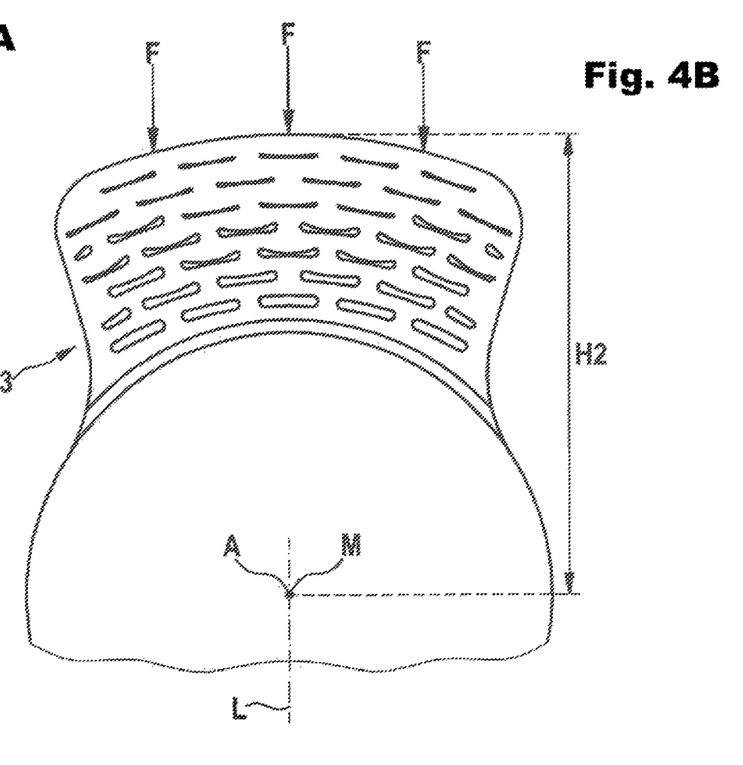
FIG. 4B shows a schematic illustration of a part of an intraocular lens according to the third embodiment in a top view in a state in which a compressive force is applied.

According to a third embodiment, further cutouts 6 can be provided, the respective centroids of which can be connected by a line that forms a further circular arc having a third radius around the center M1, wherein the further radius is smaller than the second radius R2, see FIGS. 3 and 4. The further cutouts 6 can reach up to the optics body 2, which means that the haptic body 3 has a multiplicity of cutouts 4, 5, 6, 9, 41.

It is evident from FIG. 3 that the intraocular lens 1 has an upper side 20 and a lower side 21. The first cutouts 4 and the second cutouts 5 preferably extend from the upper side 20 to the lower side 21 in the longitudinal cross section of the intraocular lens 1. Such a cutout 4, 5 is therefore an opening or a slot. Such an embodiment can be particularly advantageous for the following reason:

If an intraocular lens 1 has been inserted in a capsular bag and the latter exerts a relatively strong compressive force F in the direction of and parallel to the longitudinal axis L onto a circumferential line 12 of the intraocular lens 1 at the periphery of the haptic body 3 because the intraocular lens 1 in a relaxed state, see FIG. 4A, is too large for the capsular bag, this leads to a relatively large elastic deformation of the cutouts 4, 41, 5, and 6 in the haptic body 3, see FIG. 4B. In the relaxed state of the intraocular lens 1, a height H1 extends from the geometric center M, through which the optical axis A of the intraocular lens 1 extends in this embodiment, to the point of intersection of the circumferential line 12 with the longitudinal axis L. When a compressive force acts on the circumferential line 12, the height decreases to a height H2. The cutouts 4, 41, 5 and 6, which extend from the upper side 20 to the lower side 21, thus allow a relatively large compression similar to a sponge.

Figure 5A:
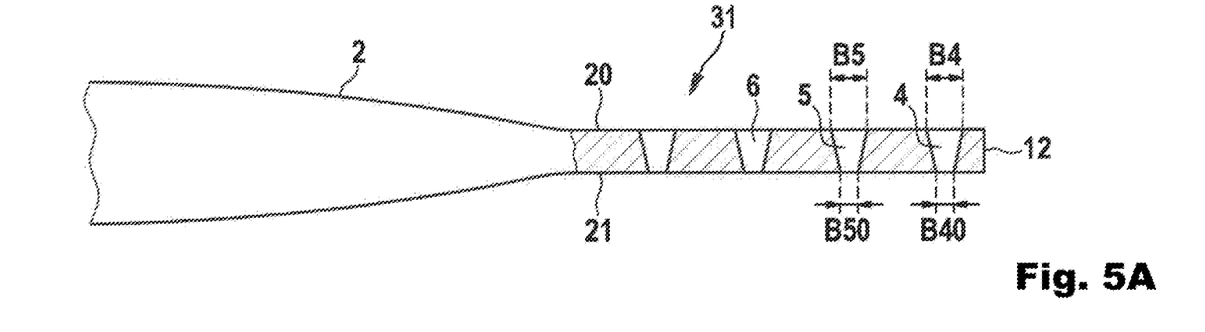
FIG. 5A shows a schematic illustration of a part of an intraocular lens according to a fourth embodiment in a longitudinal cross section in a relaxed state.
Figure 5B:
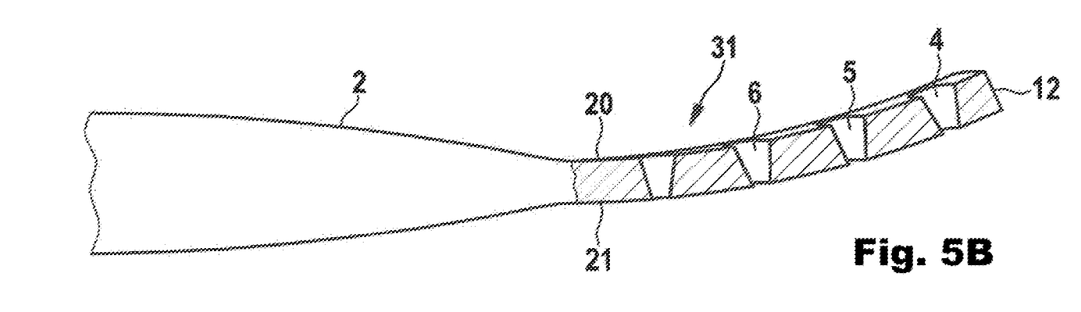
FIG. 5B shows a schematic illustration of a part of an intraocular lens according to the fourth embodiment in a longitudinal cross section in a state in which a compressive force is applied; and, FIG. 6 shows a schematic illustration of a part of a haptic body of an intraocular lens according to a fifth embodiment in a longitudinal cross section.
Figure 6:
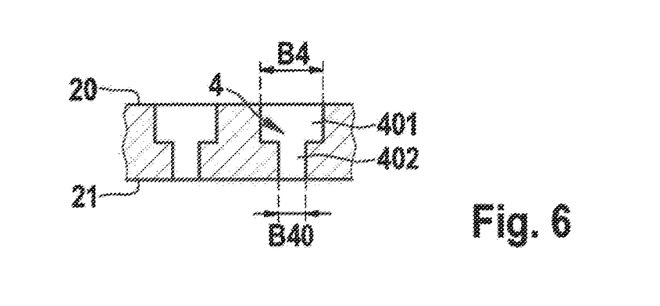

This effect can be intensified if the first cutout 4 has in the longitudinal cross section a width B4 on the upper side 20 and a width B40 on the lower side 21, wherein the width B4 on the upper side 20 is greater than the width B40 on the lower side. FIG. 5A shows such an intraocular lens 1 in the relaxed state. If a compressive force acts on the circumferential line 12 of the first haptic body 31 at the upper edge in the direction of and parallel to the longitudinal axis L, the first haptic body 31 bends toward the side on which the cutout 4 has the greater width B4, that is, toward the upper side 20, see FIG. 5B. The optics body 2 thus remains unchanged in its pose and does not undergo any axial shift along the optical axis A. The change in width from B4 to B40 can be either continuous or incremental, see FIG. 6. If this takes place in an incremental manner, the first cutout has a blind hole 401 with a width B4 which does not reach from the upper side 20 to the lower side 21, wherein this blind hole 401 is continued by another blind hole 402 having a constant width B40.

These statements also apply analogously to a second cutout 5 with a width B5 on the upper side and a width B50 on the lower side. The same also applies to the further cutouts 6.

It is understood that the foregoing description is that of the preferred embodiments of the invention and that various changes and modifications may be made thereto without departing from the spirit and scope of the invention as defined in the appended claims.

What is claimed is:
1. An intraocular lens comprising:
an optics body having a geometric center M through which a first main axis runs as a longitudinal axis L of the intraocular lens and a second main axis runs as a transverse axis Q;
said transverse axis Q being arranged perpendicular to said longitudinal axis L of the intraocular lens;
a plate-like first haptic body adjoining said optics body;
a plate-like second haptic body adjoining said optics body;
said first haptic body and said second haptic body being disposed point-symmetrically to said geometric center M;
the intraocular lens defining a circumferential line, an outer radius RA of the intraocular lens around said geometric center M, and a radial distance A1 from said geometric center M to a point of intersection of said transverse axis Q with said circumferential line;
said outer radius RA and said radial distance A1 having a ratio with respect to each other lying in a range of 1:0.5 to 1:0.9;
said first haptic body defining at least two first cutouts including a first-first cutout and a second-first cutout;
said first-first cutout being disposed on a left-hand side of the longitudinal axis;
said second-first cutout being disposed on a right-hand side of the longitudinal axis;
said first-first cutout and said second-first cutout each having a corresponding first cutout length and a corresponding first cutout width, wherein the corresponding first cutout lengths are greater than the corresponding first cutout widths;
said at least two first cutouts each having a first cutout centroid, wherein said first cutout centroids can be connected by a line forming a first circular arc having a first radius R1 around a first center M1 arranged on said longitudinal axis L;
said first haptic body defining at least two second cutouts including a first-second cutout and a second-second cutout;
said first-second cutout being disposed on said left-hand side of said longitudinal axis L;
said second-second cutout being disposed on said right-hand side of said longitudinal axis L;
said first-second cutout and said second-second cutout each having a corresponding second cutout length and a corresponding second cutout width, wherein the corresponding second cutout lengths are greater than the corresponding second cutout widths;

said at least two second cutouts each having a second cutout centroid, wherein said second cutout centroids can be connected by a line forming a second circular arc having a second radius R2 around said first center M1; and, said second radius R2 being smaller than said first radius R1.

2. The intraocular lens of claim 1, wherein at least one of said at least two first cutouts and said at least two second cutouts are formed as a slot.

3. The intraocular lens of claim 1, wherein the intraocular lens is formed from a single material.

4. The intraocular lens of claim 1, wherein at least one of said at least two first cutouts and said at least two second cutouts is disposed only within said first haptic body and does not reach an outer periphery of said first haptic body.

5. The intraocular lens of claim 1, wherein at least one of said first cutout widths and said second cutout widths are in a range from 0.05 mm to 0.8 mm.

6. The intraocular lens of claim 1, wherein the intraocular lens has an upper side and a lower side; and, at least one of said at least two first cutouts and said at least two second cutouts extend in a longitudinal cross section from said upper side of the intraocular lens to said lower side of the intraocular lens.

7. The intraocular lens of claim 6, wherein at least one of said at least two first cutouts and said at least two second cutouts has a greater width in the longitudinal cross section on said upper side of the intraocular lens than on the lower side of the intraocular lens.

\* \* \* \* \*